United States Patent [19]
DuRoss

[11] Patent Number: 5,324,751
[45] Date of Patent: Jun. 28, 1994

[54] CRYOPROTECTANT SORBITOL CRYSTAL SPHERULES

[75] Inventor: James W. DuRoss, Smyrna, Del.

[73] Assignee: ICI Americas Inc., Wilmington, Del.

[21] Appl. No.: 31,067

[22] Filed: Mar. 12, 1993

Related U.S. Application Data

[62] Division of Ser. No. 301,202, Jan. 24, 1989, abandoned.

[51] Int. Cl.$^5$ .................. A61K 31/00; A61K 47/00; C07C 29/76; C07C 29/78
[52] U.S. Cl. .................. 514/777; 568/852; 424/48; 424/439; 424/440; 424/441; 424/489; 424/606; 426/3; 426/385; 426/574; 426/657; 426/658; 426/659; 426/660; 514/23
[58] Field of Search .................. 514/23, 777; 568/852; 424/48, 439, 440, 441, 489, 606; 426/3, 385, 574, 657, 658, 659, 660

[56] References Cited

U.S. PATENT DOCUMENTS

| | | | |
|---|---|---|---|
| 3,341,415 | 9/1967 | Scott | 424/440 |
| 4,252,794 | 2/1981 | DuRoss | 514/777 |
| 4,507,511 | 3/1985 | Reiff et al. | 424/52 |
| 4,605,794 | 8/1986 | Reiff et al. | 568/852 |
| 4,661,647 | 4/1987 | Serpelloni et al. | 568/852 |
| 4,806,343 | 2/1989 | Carpenter et al. | 514/777 |

FOREIGN PATENT DOCUMENTS

| | | |
|---|---|---|
| 0111209 | 6/1984 | European Pat. Off. . |
| 3732141 | 4/1989 | Fed. Rep. of Germany . |

Primary Examiner—Ronald W. Griffin
Attorney, Agent, or Firm—Paul L. Sharer

[57] ABSTRACT

Free-flowing formations of spherules of loose knit microcrystals of the polymorphs of sorbitol and mannitol are useful in fast-frozen food products as cryoprotectants due to their improved rate of solubility and dispersion. The free-flowing formations are also helpful in formulating confectionary and pharmaceutical products by improving processing efficiencies and texture and are useful in selected industrial applications as a result of their improved rate of solution and free-flowing characteristics.

16 Claims, 3 Drawing Sheets

CRYOPROTECTANT SORBITOL CRYSTAL SPHERULES

This is a continuation of copending application Ser. No. 07/301,202 filed on Jan. 24, 1989, now abandoned.

The present invention is directed to sorbitol and sorbitol and mannitol crystalline modifications. Specifically, it is directed to free-flowing spherules of loose knit acicular microcrystals of sorbitol and combinations thereof with mannitol, sugar, and other particulate solids. It is further directed to the manufacture of food products, quick-frozen food products, confectionary products and pharmaceutical preparations employing the fast dissolving sorbitol spherules and other applications where a rapid dissolution of sorbitol is desirable to improve performance.

In the manufacture of quick-frozen foods containing water, for example, Surimi, it is desirable to process the newly harvested items rapidly and freeze them immediately to prevent degradation of the protein in such a way that they are not damaged by the formation of ice crystals within the protein micelle. In the past, many water soluble additives have been employed to lower the freezing point to eliminate ice crystal formation. Only recently, however, has it been realized that sorbitol provides sufficient cryoprotection without contributing to a distortion in natural flavor such as occurs, for example, with only sugar. Previously known crystal formations of sorbitol and mannitol, while performing well, are relatively very slow to dissolve in cold water. For greatest efficiency solid sorbitol is added directly to the aqueous food product early enough in the process to allow complete dissolution and dispersion prior to freezing. The crystal spherule formations of this invention provide a means for quickly forming cold aqueous food/sorbitol solutions/slurries and combinations thereof with sugar and other additives thereby shortening the time cycle between harvesting and freezing, while providing for improved dispersion of the cryoprotectants resulting in improved gel strength in the finished product.

It is therefore an object of the invention to provide for quick dissolving sorbitol in a free-flowing formation of loose knit microcrystals in the shape of open centered spherules. It is another object to provide co-crystalline sorbitol/mannitol microcrystals in the form of open centered spherules. It is another object of the invention to provide co-crystalline sorbitol/mannitol/sucrose microcrystals in the form of open centered spherules. Another object of the invention is to provide co-crystalline spherule products with other solid particulate additives. It is another object to provide crystalline sorbitol spherules as made by spray drying aqueous sorbitol solutions containing sorbitol seed crystals. It is another object of this invention to provide for co-crystalline sorbitol/mannitol or sorbitol/mannitol/sucrose spherules by spray drying sorbitol solutions containing sorbitol or sucrose seed crystals or combinations of the aforementioned. The invention also provides for an improved process for quick freezing aqueous food products employing sorbitol spherules. Additional products wherein sorbitol and mannitol are commonly used are also provided for.

These and other objects in the invention are better understood with reference to the figures and drawings.

Figure 1A:
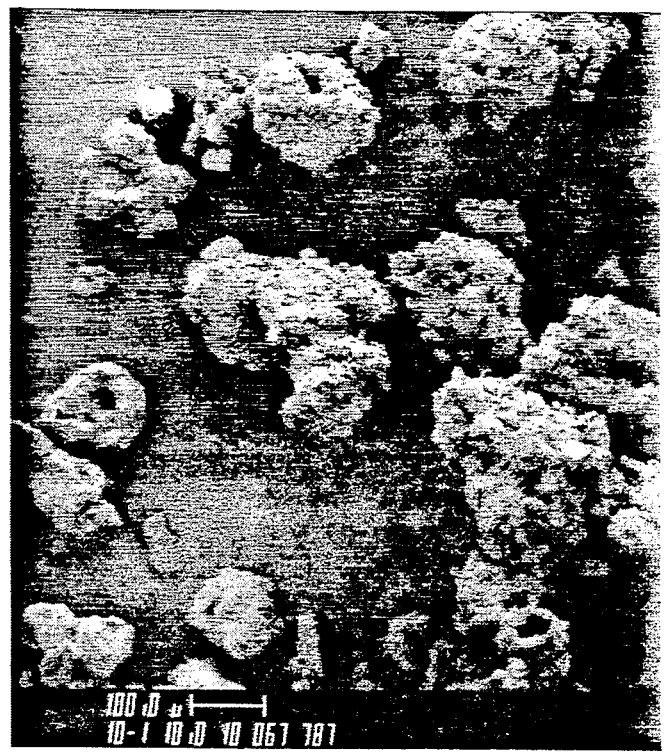
FIGS. 1a and 1b are typical scanning electron photomicrographs of a sorbitol product of the invention made according to Example 1 at magnifications of 100× and 2000× respectively.

The sorbitol or sorbitol/mannitol co-crystallized microcrystals of the invention comprise at least 60 percent gamma sorbitol and other sorbitol/mannitol polymorphs. These polymorphs are in the form of open centered, spherules of acicular microcrystals. The diameter of these spherules may range from 40 to 350 microns with an open center or less dense cavity ranging from about 10-60 microns. Individual microcrystals have thicknesses of less than about 1 micron (0.5-0.95 microns) with lengths ranging from 5-20 microns; however, some may be much larger and some much smaller.

The surface area, when measured by the Quantachrome Surface Area Analyzer based on $N_2$ Displacement Test as generally described in the article "BET Surface Area by Nitrogen Absorption" by S. Brunauer, et al, in the Journal of American Chemical Society, 60, p. 309 (1938), ranges about 1.75–5.0 $m^2$/gm. The bulk density of the material ranges from 0.3–0.7 gm/cc within the same product range delineated by surface area. The melting points as determined by Differential Scanning Colorimetry ranges from 95°–101° C. Heat of fusion values range from 34 cal/gm–44 cal/gm which correlates to a degree of crystallinity of about 60% to 100%.

The product has a significant improved rate of solution when compared to conventional sorbitol products of the past which enables it to be rapidly dissolved and dispersed in cold water. Depending upon its manufacturing history, the moisture content of the crystalline product can range from 0.5–1.5% by weight. The product distinguishes itself from prior art materials in its surface area measurement, bulk density, and its loose knit crystal arrangement in hollow centered spherules, in addition to its rapid solubility rate in cold water. For example, in comparison the melt crystallized product described in my U.S. Pat. No. 4,252,794 or a spray crystallized product similar to that described in U.S. Pat. No. 4,507,511, the relative rates of solution for a 10 gram samples in 90 mls. of deionized water at 25°, 37° and 65° C. is shown in Tables 1 and 2. Rates of solution in water at temperatures of 25°–65° C. can range from $(50-300) \times 10^{-4}$ gm/ml/sec.

In general, the product of the invention is prepared by spray drying aqueous solutions of sorbitol in the presence of crystalline sorbitol seed employing conventional commercially available spray drying equipment modified to simultaneously feed solid and liquid materials in the primary dryer.

Aqueous solutions containing about 70% by weight sorbitol or sorbitol/mannitol mixtures are readily available commercially and are usually obtained by pressure hydrogenation of aqueous dextrose using a Raney nickel catalyst. Solutions containing nearly pure sorbitol or solutions with up to about 20% by weight mannitol based on the total weight of the solids are readily available depending on the starting materials; catalysts and techniques employed in their manufacture. The purity of the sorbitol solution with regard to the mannitol, sorbitol and other isomeric sugar alcohols such as iditol, galactitol or talitol is not considered critical in the formation of the spray dried product of the invention. It is preferred, however, that the sorbitol solution be filtered and clear and free of insoluble impurities derived from the hydrogenation process. Saturated-aqueous sorbitol solution containing from about 60–80% by weight total solids is considered operable in the spray drying process; however, those solutions containing about 65–70% by weight solids are most available.

The spherules of the invention are obtained by co-spraying saturated aqueous sorbitol solutions or sorbitol/mannitol solutions with microcrystals of sorbitol or sorbitol/mannitol seed blends. It is preferred that the cross-sectional dimensions of the microcrystals used for seed range from 0.5 to 1 microns in width and 20–50 microns in length. Such seed is obtained either by grinding and sifting product from melt crystallization, aqueous crystallization or directly as recycled from the spray drying process. In most instances, particles which pass through a 120 mesh screen U.S. sieve series (125 microns) are operable. The amount of seed particles added with the spray drying process need not exceed an equal volume of sorbitol liquid. On a weight basis, the amount of seed per weight solids in the aqueous solution may range from 1.0–1.4 depending upon the feed rate, air volume, air velocity, and operating temperatures of the spray dryer employed.

In commingling the seed with the aqueous sorbitol solution prior to entering the spray dryer, several conventional techniques are employed. When jet spray equipment is used, high pressure spray jets form liquid droplets forcing them into a seed fog as they enter the dryer. In another technique, the seed is instantly mixed with the liquid prior to entering the high pressure jets. It is preferred, however, to add the seed to the liquid immediately before it passes into a high velocity rotary atomizer operating at a pressure of about 50–100 MPa. With this technique, droplets ranging from about 50–1000 microns and preferably 250–300 microns are introduced into a high temperature vortex of heated air (140°–200° C., and preferably about 140°–160° C.). The instant pressure differential creates a droplet having the approximate shape of a mushroom cap from which moisture is rapidly evaporated permitting concentrated sorbitol solution to crystallize on the seed particle to create a spherule of loose knit microcrystals as it falls through the spray dryer. While the microcrystals are being formed, they bond to one another sufficiently such that the hollow centered spherule remains intact, thus creating a free-flowing bed of spherules which flow out of the dryer with a moisture content no greater than about 5–8% by weight depending upon the drying rate used.

Figure 3:
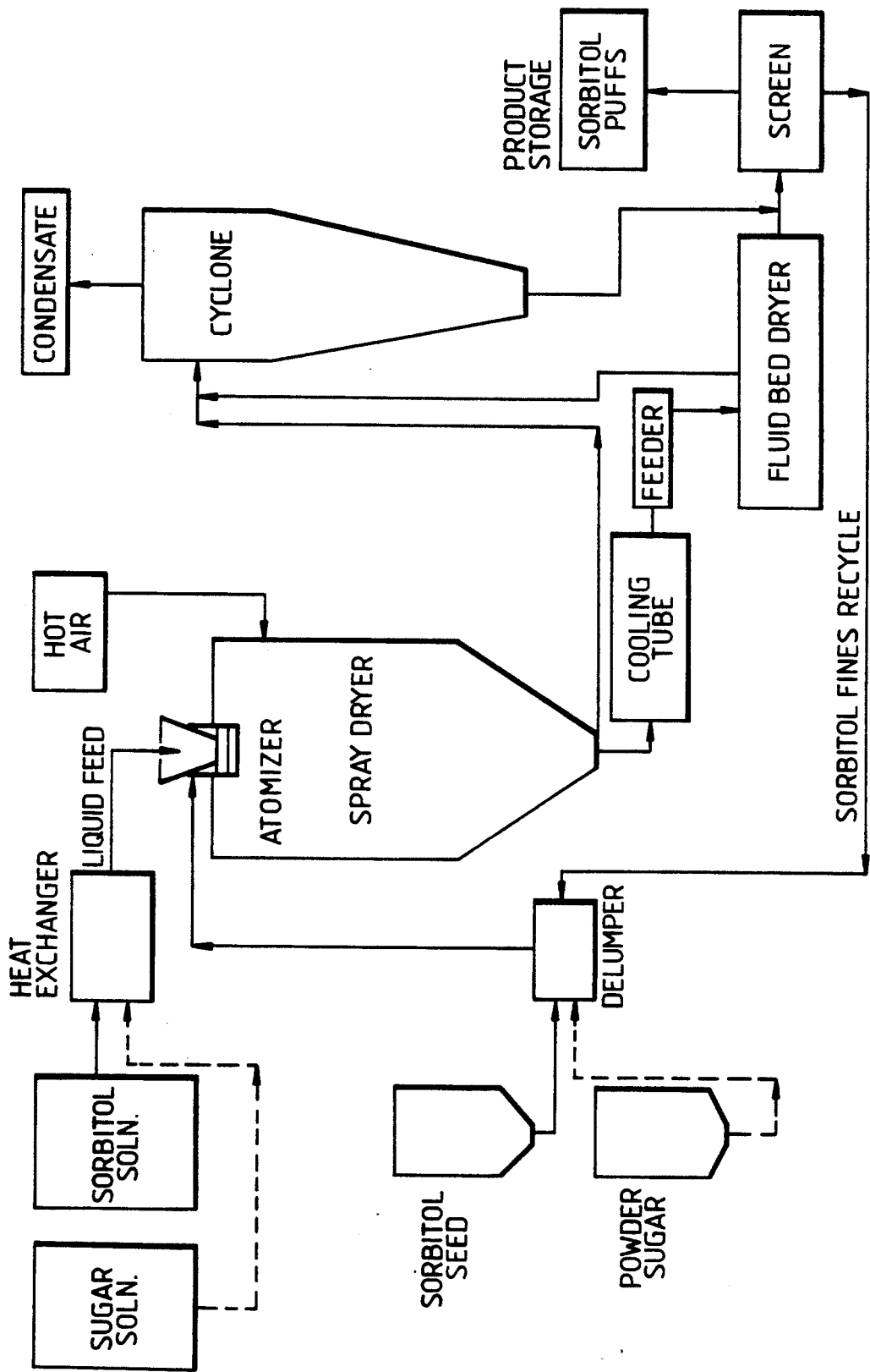
FIG. 3 is a line drawing showing a typical box flow diagram for producing the products of the invention by a spray drying technique which further incorporates solid feed co-spraying means.

The product of the invention is made in conventional commercially available spray drying equipment and an understanding of its operation is better understood with reference to the labeled box flow diagram of FIG. 3 in connection with the following general operating procedure which provides a nonlimiting basis for the nonlimiting examples which follow.

GENERAL OPERATING PROCEDURE

Tonnage quantities of aqueous sorbitol or sorbitol/mannitol blends are held in a heated tank at temperatures ranging from 37°–49° C. and pumped through a heat exchanger (optional) such that the liquid is heated to a temperature of 80°–85° C. in a period less than about 6 seconds where it is fed directly into a rotary atomizer operating at pressures of 50–100 MPa.

Figure 1B:

Tonnage quantities of particulate sorbitol seed are held in a vibrating hopper and passed through a delumping machine after which it is metered directly into the vortex of the rotary atomizer along with liquid feed, wherein it is mixed and spun out under high pressure through the orifice of the atomizer and sprayed into the hot air vortex created in the upper section of a cylindrical spray dryer having an approximate diameter of about 6 meters and a depth of about 18.5 meters. Upon entering the high velocity stream of air, the droplet is immediately spread out into a thin film and then into a mushroom cap shape to develop the hollow center as a function of the density of the liquid and its velocity and the velocity of the air. The droplet puffs out as water vapor is emitted from the droplet surface which increases with temperature. Simultaneously therewith, rapid microcrystals are formed in the supersaturated seeded droplet to generate a multitude of microcrystals bonded to one another at their point of contact to form loose knit crystal spherules as shown in photomicrographs FIGS. 1b and 2b. The crystal puff formation takes place primarily in the upper 6 meter portion of the spray dryer in the vortex of swirling particles created by the high velocity air stream entering tangentially at temperatures of about 140°–160° C. Air volume is regulated between 2500–3500 cubic meters having a density of 0.854–0.815 kilograms per cubic meter. As the particles fall through the lower 12 meters of spray dryer, water is continually removed at an evaporation rate of 150–200 kilograms/hour from the mass of spherules which are removed at a moisture content ranging from 2–10% and preferably about 5% on exiting the dryer.

Powder flowing from the bottom of the dryer enters a cooling tube at its base prior to entering a fluid bed dryer. The cooling tube is optional and its use depends on the temperate differential between product entering the spray dryer and the first zone of the fluid bed dryer wherein a stream of air moves through the bed of powder to remove unbound moisture. Normally, the fluid bed dryer has 3 to 4 zones each one fluidized with lower temperature air and varying air velocities. Due to the heat sensitivity of sorbitol, the air temperature and velocity must be such that the surface temperature of the spherule is held below 94° C. to avoid melting, softening and clumping. The fluid bed dryer normally lowers the moisture content to below 1.5%, preferably less than 1.0% based on total product weight.

Product leaving the fluid bed dryer is passed through a screen or sifter where agglomerates are broken. Appropriate sized screens are used to manufacture a desired particle size before placing in storage containers. Coarse powder is screened off, reground and delivered to the fines recycle stream and are conveyed back to the seed feed stream. Fines or dust is screened off and delivered as such to the recycle stream back to the seed feed stream. The free-flowing product is stored in moisture proof drums or bags.

Air passing out of the spray dryer is passed through a cyclone separator and/or bag house to remove fines which can thereafter be delivered to the fines recycle hopper and used as seed material.

EXAMPLE 1

According to the general procedure described above, 70% sorbitol solution (SORBO®—ICI Americas Inc.), mixed with sorbitol seed particles (+360 mesh) on a solid basis of 1.4/1 (liquid sorbitol/seed) and is fed at the combined rate of about 680 kilograms per hour. Sorbitol leaving the tank is heated to 43°-46° C. and preheated to a temperature of about 82° C. Sorbitol seed particles are fed at room temperature. The operating pressure at the mixing chamber is held at 75-85 MPa. The dryer is operated at an air temperature of 140°-160° C. with an approximate evaporation rate of about 150 kgs./hour.

The product may be characterized as follows:

| Melting Point °C. | 98.88 (1 polymorph) |
|---|---|
| Heat of Fusion | 186.2 J/gm |
| Surface Area | 3.92 m²/gm |
| Bulk Density | 0.36 gm/cc |

Rate of solution is determined by placing 90 mls of deionized water in 150 ml glass beaker, then dropping 10 grams sorbitol product −20/+60 mesh (U.S. Sieve Series) in a vortex created by a magnetic stirrer turning at 50-70 RPM. Water temperature is measured immediately before drop. Time of dissolution is measured from instant of drop to instant of visual disappearance of solid material in the beaker. Rates are calculated according to the formula:

gms (sorbitol/powder)/mls (deionized water)/time in seconds to complete solution

TABLE 1

| Powdered Sorbitol | Solution Time (secs) | | | Rate of Dissolution (gms/ml/sec) × $10^{-4}$ | | |
|---|---|---|---|---|---|---|
| | Temperature °C. | | | | | |
| | 25° | 37° | 65° | 25° | 37° | 65° |
| Example 1 | 14 | 5 | 4 | 79 | 222 | 278 |
| U.S. Pat. No. 4,252,794 | 187 | 11 | 10 | 6 | 101 | 111 |
| U.S. Pat. No. 4,507,511 | 39 | 9 | 8 | 20 | 123 | 139 |

EXAMPLE 2

According to the procedure of Example 1, an aqueous solution containing 58% by weight sorbitol and 10% by weight mannitol is fed at a ratio of 1/1 (liquid/seed) under similar operating conditions.

The product may be characterized as follows:

| Melting Point | 71.67° C./96.83° C. (2 polymorphs) |
|---|---|
| Heat of Fusion | 5.604/146.7 J/g |
| Surface Area | .410 gm/cc |
| Bulk Density | 3.51 m²/gm |
| Rate of Dissolution at | 25.6° C. |

TABLE 2

| Powdered Sorbitol | Time (Seconds) | Rate of Dissolution in Water (25° C.) (gms./ml./sec.) × $10^{-4}$ |
|---|---|---|
| Example 2 spherules | 16 | 69 |
| Product U.S. Pat. No. 4,252,794 | 206 | 5 |
| Product U.S. Pat. No. 4,507,511 | 52 | 28 |

Figure 2A:
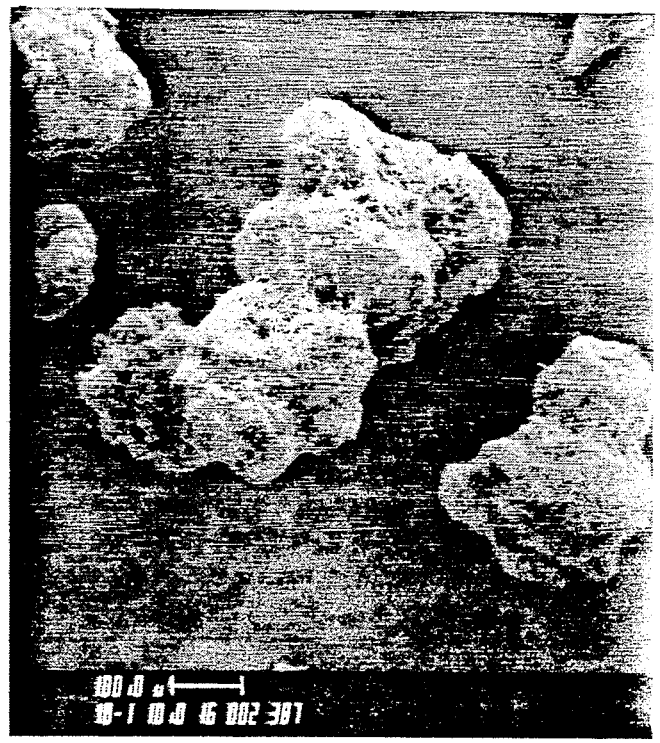
FIGS. 2a and 2b are typical scanning electron photomicrographs of a sorbitol/mannitol product of the invention made according to Example 2 at magnifications of 100× and 2000× respectively.
Figure 2B:
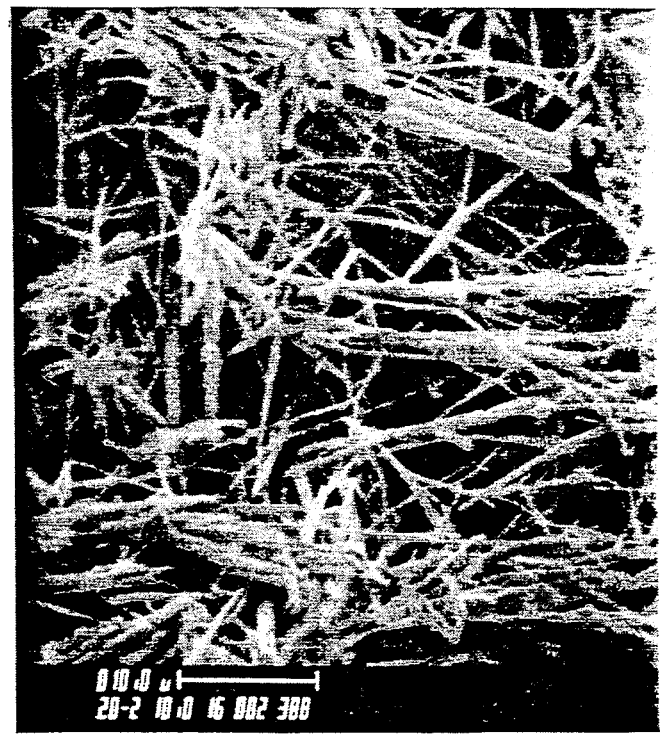

Photomicrographs of FIGS. 2a and 2b indicate that the spherules can be slightly agglomerated, and the less dense open center is not always visible in the granule.

The products of the invention are particularly useful as a cryoprotectant when employed in the treatment of fresh foods which are to be frozen. One particular use is in the production of Surimi, a Japanese term for mechanically deboned fish flesh that has been washed with water to form a protein gel from fish such as Alaskan Pollock or Hake. In the manufacture of this product, fish caught at sea are taken to a factory ship wherein fish are descaled, filleted, the protein extracted and mixed with cryoprotectant and quickly frozen in the shape of 10 kilogram blocks which are stored until off-loaded. Crystalline sorbitol is used as a cryoprotectant along with, in some instances, sucrose to prevent degradation of the protein gel due to freezing of the water within the protein micelle when the Surimi is blast-frozen to −20° C. or lower. During processing, there is a limited amount of time for the cryoprotectants to be added, dissolved and become thoroughly dispersed within the Surimi gel to be frozen. If the cryoprotectant is not totally dissolved and/or thoroughly dispersed, it will not provide the necessary protection and will result in reduction of protein functionality on freezing, storing, defrosting.

The protein gel has been used as a protein supplement and can be mixed with other additives such as modified starches, stabilizers, other proteins, sugars, emulsifiers, coloring agents and flavors then woven or extruded into finished analog products such as imitation crab meat, imitation lobster meat, imitation chicken and imitation lunchmeats. In general, all other variables held constant, the quality of the frozen Surimi is inversely proportional to the time lapse between the harvesting of the fish and freezing and directly proportional to the distribution of the cryoprotectant in the product.

The sorbitol spherules of the invention can be added to fish protein gel in concentrations ranging from 2-10% by weight as the sole cryoprotectant or in combination with equal amounts of sucrose at the 4% level and small amounts of other additives such a sodium polyphosphate. Because the microcrystalline spherules dissolve instantaneously in the fish protein gel as it is manufactured, no delay is encountered in the mixing process and the cryoprotectant is allowed to become more thoroughly dispersed. All other variables being equal, Surimi processed with the sorbitol crystal spherules of the invention are expected to be of higher quality than those using slower dissolving sorbitols of the prior art. Grade 1 gel strengths are easily obtained upon thawing.

Other time savings and improvements in the functional properties of the gel are realized by adding blends of the sorbitol spherules with other commonly used ingredients such as sugar and sodium tripolyphosphate or sodium pyrophosphate. For example, powdered 10X sugar can be added in the spray drying process along with the seed crystals or as aqueous concentrated sucrose solution along with sorbitol solution at the jets or atomizer.

EXAMPLE 3

According to the procedure of Example 1, 70% solids/sucrose/sorbitol (weight ratio of 1:1) solution is metered at 82° C. into the rotary atomizer at a ratio of 1.4 to 1 sugar/sorbitol to seed.

EXAMPLE 4

According to a procedure similar to Example 1, 10× sugar is passed through a delumper and mixed with sorbitol seed and fed into the rotary atomizer at room temperature along with aqueous sucrose/sorbitol (1. to 1.) at a weight ratio of 1.4/1 (sugar/sorbitol to seed) and processed accordingly.

EXAMPLE 5

The product of Example 4 is blended in a V-type solid mixer with sodium tripolyphosphate to form a blend containing sugar/sorbitol/polyphosphate in a weight ratio of 48/48/4 and packaged in moisture proof containers.

EXAMPLE 5a

The product of Example 1 or 2 is blended in a V-type solids mixer with sucrose and/or sodium tripolyphosphate in a weight ratio of sorbitol (Example 1) or sorbitol/mannitol (Example 2) to form a blend containing 48% sucrose/48% sorbitol/4% sodium tripolyphosphate or 48% sucrose/48% sorbitol/mannitol/4% tripolyphosphate.

EXAMPLE 6

Improved Surimi is manufactured by the process of incorporating the products of Examples 1-5 into the protein gel mix manufactured from Alaskan Pollock according to a commercial process outlined by C. M. Lee in *Food Technology*, pgs. 69-80 (November 1984) at concentrations represented in Table 3. Spun protein made according to these formulations can be used to make analogs of crab meat, lobster meat and other fish products.

TABLE 3

| Surimi (Alaskan Pollock) | | |
|---|---|---|
| Cryoprotectant | Concentration in Gel | Added Polyphosphate |
| Example 1 | 8% | .13% |
| Example 2 | 8% | .2% |
| Example 3 | 8% | .15% |
| Example 4 | 7.5% | .3% |
| Example 5 | 8% | 0 |
| Example 1 + sucrose | 4 + 4% | 0 |
| Example 2 + sucrose | 4 + 4% | .15% |

EXAMPLE 7

| Surimi | |
|---|---|
| Protein | 10-20% |
| Water | 2-4% |
| Product of Example 1 | 2-4% |
| Sucrose | 68-86% |
| Sodium TriPolyphosphate | 1-4% |
| OR | |
| Surimi (Alaskan Pollock) (Protein/water gel) | 88-95% |
| Sucrose | 2-4% |
| Product of Example 1 | 2-4% |
| Sodium TriPolyphosphate | 1-4% |

Improvements Noted

1. Improved solubility of cryoprotectant in Surimi
2. Improved dispersibility of cryoprotectant in Surimi
3. Reduced syneresis of protein gel
4. Stronger protein gels on defrosting
5. More latitude in formulating Surimi-based products due to strength of protein gel
6. Reduce loss of Surimi product due to inadequate gel strength representing significant financial savings to processor

EXAMPLE 8

| Imitiation Crab Meat | |
|---|---|
| Surimi | 40.0% |
| Starch (modified) | 4.5% |
| Sucrose | 5.0% |
| Product of Example 1 | 5.0% |
| Egg White (dried) | 2.0% |
| Salt | 3.0% |
| Flavor enchancer | 0.5% |
| Shellfish flavor (dried) | 1.0% |
| Shellfish meat | 39.0% |

Improvements Noted

1. Improved solubility of cryoprotectant in analog
2. Improved texture due to:
   - Protein gel strength
   - No grit from undissolved cryoprotectant
3. Reduced cost of analog product to consumer
4. Greater formulation latitude due to improved gel strength In addition to frozen food processing, advantageous use of the microcrystalline sorbitol spherules of the invention is realized in confectionary products such as candy, chewing gum, chocolate coatings, chewable tablets and pharmaceutical excipients in tablet form and/or powders. In chocolate coatings, for example, 40-60% replacement of sugar, sorbitol and/or mannitol is obtainable with improved textures. Hard confectionary tablets having improved texture, hardness and faster dissolution can be made by combining commercially available, slow dissolving (less than $40 \times 10^{-4}$ gm/ml/sec at 25° C.) sorbitol with 40-99% by weight of the spherules of this invention. Likewise, 30-90% of granular sorbitol and mannitol employed in chewable tablets can be replaced by the spherules of this invention. Even though the product of the invention is difficult to tabletize alone (by itself) for the manufacture of hard confectionary tablets, improvements in tablet hardness are surprisingly obtained when combined with the larger, coarse particle sized crystals known previously.

Further improvements in the manufacture of chewing gum having improved texture and flavor are obtained when manufactured from the sorbitol spherules of the invention. Further benefits are obtained in the processing of gum compositions in that the microcrystalline particles are more easily dispersed in gum bases normally employed in commercial gum manufacture.

The following nonlimiting examples serve to illustrate but not limit the many applications intended in the manufacture of confectionaries, tablets, chewing gum and pharmaceutical formulations.

EXAMPLE 9

| Sucrose-free Chocolate Coating | |
|---|---|
| Chocolate liquor | 56.00% |
| Product of Example 2 | 42.55% |
| Lecithin | 0.50% |
| Sorbitan monostearate | 0.60% |
| Saccharin | 0.10% |

-continued

| Sucrose-free Chocolate Coating | |
|---|---|
| Vanillin | 0.25% |

EXAMPLE 9a

| Hydrogenated Palm Oil (105° FMP) | 25.00 |
|---|---|
| Product of Example 1 | 53.00 |
| Cocoa Powder (11% C.B.) | 15.00 |
| Cocoa Butter | 5.5 |
| Lecithin | 0.50 |
| Sorbitan monostearate | 0.60 |
| Saccharin | 0.10 |
| Vanillin | 0.30 |

Benefits

1. Smoother textured chocolate coating; no grit
2. Improved milling characteristics; reduced roll wear
3. Improved color, gloss
4. Improved mixing, processing
5. Reduced formulation cost versus mannitol

EXAMPLE 10

| Carrier for Powdered Flavors; Sweeteners | | |
|---|---|---|
| ° | Powdered lemon flavor: | 10% |
| | Product of Example 1 | 90% |

Dry blend 15 minutes; V Blender

EXAMPLE 10a

| ° | Aspartame ® | 25% |
|---|---|---|
| | Product of Example 2 | 75% |

Dry blend 15 minutes; V Blender

Benefits

1. More uniform dispersion of artificial flavors and/or sweetener throughout tablet granulation
2. Better flavor perception due to uniformity of dispersion
3. Less expensive than other carriers
4. Reduces need for aqueous phase to bind product to the carrier

EXAMPLE 11

| Sucrose-free Chewing Gum | |
|---|---|
| Gum Base (Paloja ®) | 25.00% |
| Sorbitol Solution (70%) | 20.00% |
| Powder of Example 1 | 52.90% |
| Glycerine | 0.50% |
| Flavor | 1.50% |
| Aspartame ® | 0.10% |

EXAMPLE 11a

| Gum Base (Paloja ®) (Drefus Co.) | 25.00% |
|---|---|
| Hydrogenated Starch Hydrolysate | 7.00% |
| Powder of Example 2 | 59.00% |
| Glycerine | 7.00% |
| Flavor | 1.50% |

-continued

| Saccharin | 0.50% |
|---|---|

Benefits

1. Softer, more extrudable gum as made
2. No grit, better textured gum
3. No lumps of hard sorbitol in gum; less scrap
4. Improved shelf life as measured by stick flexibility; product acceptance

EXAMPLE 12

| Sucrose-free Tablet | |
|---|---|
| Crystalline Sorbitol | 48.80% |
| (−40/+200 U.S. Sieve Series) | |
| Product of Example 2 | 48.70% |
| Magnesium Stearate | 1.50% |
| Flavor; Peppermint | 1.00% |

EXAMPLE 12a

| Crystalline Sorbitol | 60.00% |
|---|---|
| (−20/+60 U.S. Sieve Series) | |
| Product of Example 1 | 37.50% |
| Magnesium Stearate | 1.50% |
| Flavor; Peppermint | 1.00% |

Benefits

1. Imparts better flow to granulation
2. Reduced dust in granulation; reduced maintenance
3. Produces harder tablet when blended in with other commercial sorbitol powders
4. Improves texture by reduction in grit
5. Provides mechanism for more even distribution of artificial flavors/sweeteners throughout granulation/finished tablet

EXAMPLE 13

| Carrier for Pharmaceutical Active: | | |
|---|---|---|
| ° | Sodium Fluoride | 10% |
| | Product of Example 1 | 90% |

Dry blend 15 minutes; V Blender

EXAMPLE 13a

| ° | Phenylpropanolamine HCL | 20% |
|---|---|---|
| | Product of Example 1 | 80% |

Dry blend 15 minutes; V Blender

Benefits

1. Reduced segregation in granulation
2. Improved assay of active in finished product
3. Reduced formulation cost

EXAMPLE 14

| Pharmaceutical Powders | | |
|---|---|---|
| ° | Aspirin | 325 mg |
| | Product of Example 1 | 325 mg |

-continued

| Pharmaceutical Powders | |
|---|---|
| Saccharin | 5 mg |

EXAMPLE 14a

| | | |
|---|---|---|
| o | Acetaminophen (coated) | 500 mg |
| | Product of Example 2 | 650 mg |
| | Saccharin | 15 mg |

Dry blend in V-belnder for 10 minutes and package in individual papers.

Benefits

1. Significantly reduced costs versus mannitol
2. Significantly improved rate of dissolution in water
3. Improved mouthfeel of analgesic solution

EXAMPLE 15

| Glass Etching Compound | |
|---|---|
| Product of Example 1 | 50.00 |
| Hydrofluoric Acid | 50.00 |

Benefits

1. Improved rate of solution
2. Reduced caking
3. No streaking of glass

EXAMPLE 16

| Wall Joint Compound | |
|---|---|
| Gypsum | 40-80% |
| Adhesive/Binder | 15-20% |
| Product of Example 2 | 2-10% |

Benefits

1. Improved flow of product
2. Reduced caking
3. Improved solution/spreadability of paste

What is claimed is:

1. Fast dissolving, free-flowing polymorphs selected from sorbitol and sorbitol/mannitol blends in the form of open centered spherules of acicular microcrystals, said microcrystals having thicknesses of less than about 1 micron with lengths ranging from 5-20 microns and wherein said spherules range in diameter from 40-350 microns with open centered cavities ranging from about 10-60 microns in cross-section.

2. Spherules of claim 1 having surface areas ranging from 1.75-5.0 $m^2/gm$ and a bulk density in the range of 0.3-0.7 gm/cc.

3. The spherules of claim 1 having a solubility rate in water at a temperature of 25°-65° C. of $(50-300) \times 10^{-4}$ gm/ml/sec.

4. A blend comprising the crystal spherules of claim 1 and powdered sugar.

5. A blend of claim 4 when made by the process of spray drying a saturated aqueous solution of sorbitol and sugar containing microcrystals of sorbitol seed.

6. A blend of claim 4 when made by the process of spray drying a saturated solution of sorbitol containing microcrystals of sorbitol seed and powdered sugar.

7. A blend of claim 4 further comprising sodium tripolyphosphate.

8. A quick frozen food product processed with the crystal spherules of claim 1.

9. The product of claim 8 comprising a protein gel derived from fish.

10. Analog food products derived from the frozen protein gel of claim 9.

11. A confectionary comprising the crystal spherules product of claim 1.

12. A product of claim 11 selected from the group consisting of chocolate coatings, hard candy, chewable tablets and chewing gum.

13. A pharmaceutical composition comprising the crystalline product of claim 1.

14. A hard, compressed tablet comprising slow dissolving sorbitol powder having a solubility rate in water at 25° C. of less than $40 \times 10^{-4}$ gm/ml/sec and 30-98% by weight of crystal spherules of claim 1.

15. A chewable tablet comprising slow dissolving sorbitol powder and 30-90% by weight of spherules of claim 1.

16. Fast dissolving, free-flowing polymorphs selected from sorbitol and sorbitol/mannitol blends in the form of open centered spherules of acicular microcrystals, said microcrystals having thickness of less than about 1 micron with lengths ranging from 5-20 microns and wherein said spherules range in diameter from 40-350 microns with open centered cavities ranging from about 10-60 microns in cross-section made by the process of spray drying saturated aqueous sorbitol or sorbitol/mannitol solutions containing microcrystals of sorbitol seed.

* * * * *